(12) United States Patent
Macey

(10) Patent No.: US 6,579,296 B1
(45) Date of Patent: Jun. 17, 2003

(54) METHOD AND APPARATUS FOR CLAMPING

(76) Inventor: Theodore I. Macey, 1212 Twin Bay Dr., Ft. Walton Beach, FL (US) 32547

( * ) Notice: Subject to any disclaimer, the term of this patent is extended or adjusted under 35 U.S.C. 154(b) by 0 days.

(21) Appl. No.: 09/581,845

(22) PCT Filed: Mar. 12, 1999

(86) PCT No.: PCT/US99/05456

§ 371 (c)(1),
(2), (4) Date: Jun. 19, 2000

(87) PCT Pub. No.: WO99/45856

PCT Pub. Date: Sep. 16, 1999

(51) Int. Cl.[7] ................................................ A61F 5/00
(52) U.S. Cl. ........................................................ 606/86
(58) Field of Search ............................ 606/53, 54, 55, 606/57, 59, 60, 61, 62, 64, 69, 71, 72, 73, 86, 87, 95, 96

(56) References Cited

U.S. PATENT DOCUMENTS

| | | | |
|---|---|---|---|
| 331,812 A | 12/1885 | Norris | |
| 1,428,679 A | 9/1922 | Caswell | |
| 2,427,128 A | 9/1947 | Ettinger | |
| 2,631,585 A | 3/1953 | Siebrandt | |
| 4,146,022 A | 3/1979 | Johnson et al. | |
| 4,706,660 A | * 11/1987 | Petersen | ............... 128/92 VW |
| 5,129,908 A | 7/1992 | Petersen | |
| 5,253,554 A | 10/1993 | Riera et al. | |
| 5,284,482 A | 2/1994 | Mikhail | |
| 5,312,403 A | 5/1994 | Frigg | |
| 5,607,344 A | 3/1997 | Endres | |
| 5,735,857 A | 4/1998 | Lane | |
| 5,853,211 A | * 12/1998 | Sawdon et al. | ............... 294/116 |
| 5,968,051 A | * 10/1999 | Luckman et al. | ............... 606/88 |

* cited by examiner

Primary Examiner—Michael J. Milano
Assistant Examiner—Vy Q. Bui
(74) Attorney, Agent, or Firm—Andrew F. Reish

(57) ABSTRACT

A clamping apparatus (10) for stabilizing a support material (20) includes a first clamping jaw (14) having a first aperture (28), a second clamping jaw (16), a mechanism (56) for pivoting the first clamping jaw (14) relative to said second clamping jaw (16), and a mechanism (18) for substantially reducing surface discontinuities on a support material (20) while enhancing friction between itself and the support material (20). The discontinuity reducing mechanism (18) includes a second aperture (36), and a mechanism (26) for attaching the discontinuity reducing mechanism (18) to the first clamping jaw (14) where the first aperture (28) is substantially aligned with the second aperture (36).

23 Claims, 2 Drawing Sheets

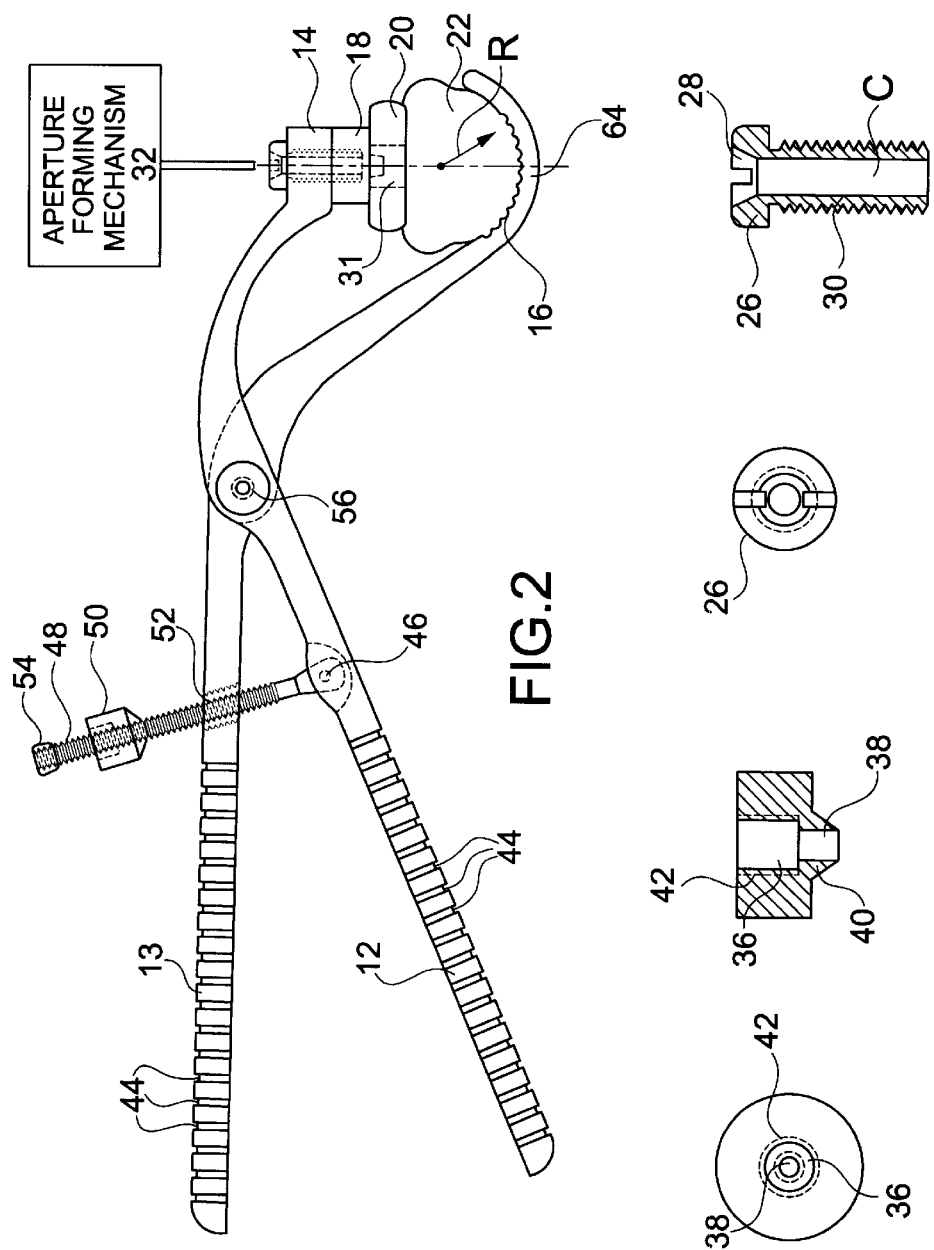

METHOD AND APPARATUS FOR CLAMPING

BACKGROUND OF THE INVENTION

1. Technical Field of the Invention

The present invention relates to a method and apparatus for clamping a support or reinforcement material to a working material. The clamping apparatus employs first and second clamping jaws which grasp a working material. The first clamping jaw includes means for substantially reducing surface discontinuities on a support or reinforcement material while enhancing friction between the discontinuity reducing means and the support reinforcement material.

2. Description of the Background Art

Various clamping devices currently exist. These clamping devices use clamping jaws with pivotable members that include serrated or rough engagement surfaces. For example, bone clamp and plate holding systems by LINK™ provide first and second curved and rigid serrated clamping jaws where the first curved serrated clamping jaw is pivotable relative to the second stationary curved serrated clamping jaw. When the first curved pivotable serrated clamping jaw is used to hold a support material such as a bone plate on top of a working material such as bone, the first serrated and curved clamping jaw tends to create surface discontinuities such as scratches on the support material (bone plate) which in turn causes stress risers or stress concentrations in the support material in regions in the vicinity of the scratches. The stress risers or stress concentrations in the support material (bone plate), particularly within an environment such as inside living tissue, can lead to failure of the plate and inadequate support of the working material (minimizing further fracture of a bone structure).

Accordingly, a need in the art exists for a method and apparatus for clamping which substantially reduces surface discontinuities on a support material while enhancing friction between the clamping device and the support material.

SUMMARY OF THE INVENTION

Accordingly, it is a primary object of the present invention to provide a method and apparatus for clamping which substantially reduces surface discontinuities on a support material while enhancing friction between the clamping apparatus and the support material. The clamping apparatus further includes mechanisms that facilitate cleaning and sterilization of the clamp.

It is a further object of the present invention to hold a support or reinforcement material in a predetermined position while maintaining adequate support for a working material to substantially prevent further fracturing that may be present in the working material.

Another object of the present invention is to provide a method and clamping apparatus where the clamping device can engage apertures of a support or reinforcement material and prevent slipping and movement of the support or reinforcement material while substantially reducing the size of fractures present in a working material.

Another object of the present invention is to substantially reduce the formation of scratches or other surface discontinuities which in turn create stress concentrations or stress risers in the vicinity of the scratches in the support material which can lead to failure of the support material.

It is further an object of the present invention to provide a method and mechanism for substantially reducing surface discontinuities on the support material while enhancing friction between the discontinuity reducing mechanism and the support material.

It is a further object of the present invention to provide a method and apparatus for substantially reducing surface discontinuities on a support material while enhancing friction between the discontinuity reducing mechanism and the support material and where the discontinuity reducing mechanism includes at least one of a substantially planar and a predetermined shaped surface which matches the shape of a support or reinforcement material.

Another object of the present invention is to provide a method and apparatus for substantially reducing surface discontinuities on the support material while enhancing friction between the discontinuity reducing mechanism and the support material in addition to aligning an aperture forming mechanism with an aperture in the first clamping jaw, an aperture in the mechanism for substantially reducing surface discontinuities, and an aperture in a support or reinforcement material.

It is a further object of the present invention to provide a method and apparatus for clamping where the clamping apparatus can be locked into a position where a support or reinforcement material is held adjacent to a working material.

Another object of the present invention is to provide a method and apparatus for clamping which guides the movement of an aperture forming mechanism through a support or reinforcement material in addition to a working material and through apertures in first and second clamping jaws of the clamping apparatus.

A further object of the present invention is to provide first and second handles of a clamping apparatus which move in a smooth motion relative to each other while carrying the sheer load from a force generated from a support or reinforcement material held adjacent to a working material.

These and other objects of the present invention are fulfilled by providing a method of clamping comprising the steps of providing a clamping device with a first clamping jaw and a second clamping jaw; attaching a traction material to the first clamping jaw; grasping a first side of the working material with the second clamping jaw; pressing a support material against a second side of the working material using the traction material, the traction material substantially reducing formation of surface discontinuities on the support material while enhancing friction between the traction material and the support material; and aligning an aperture in the first clamping jaw with an aperture in the traction material.

In addition, these and other objects of the present invention are also accomplished by providing a clamping apparatus for stabilizing a support material comprising a first clamping jaw having a first aperture; a second clamping jaw; means for providing the first clamping jaw relative to the second clamping jaw; means for substantially reducing surface discontinuities on the support material while enhancing friction between the discontinuity reducing means and the support material, the discontinuity reducing means including a second aperture; and means for attaching the discontinuity reducing means to the first clamping jaw, the first aperture being substantially aligned with the second aperture.

Further scope of applicability of the present invention will become apparent from the detailed description given hereinafter. However, it should be understood that the detailed description and specific examples, while indicating preferred embodiments of the invention, are given by way of

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 is a side view of the clamping apparatus of the present invention;

FIG. 3A is an elevational view of a mechanism for substantially reducing formation of surface discontinuities on a support material;

FIG. 3B is a cross-sectional view of the mechanism for substantially reducing formation of surface discontinuities on a support material;

FIG. 4A is an elevational view of a fastener mechanism; and

FIG. 4B is a cross-sectional view of the fastener shown in FIG. 4A.

DETAILED DESCRIPTION OF THE PREFERRED EMBODIMENTS

Figure 1:
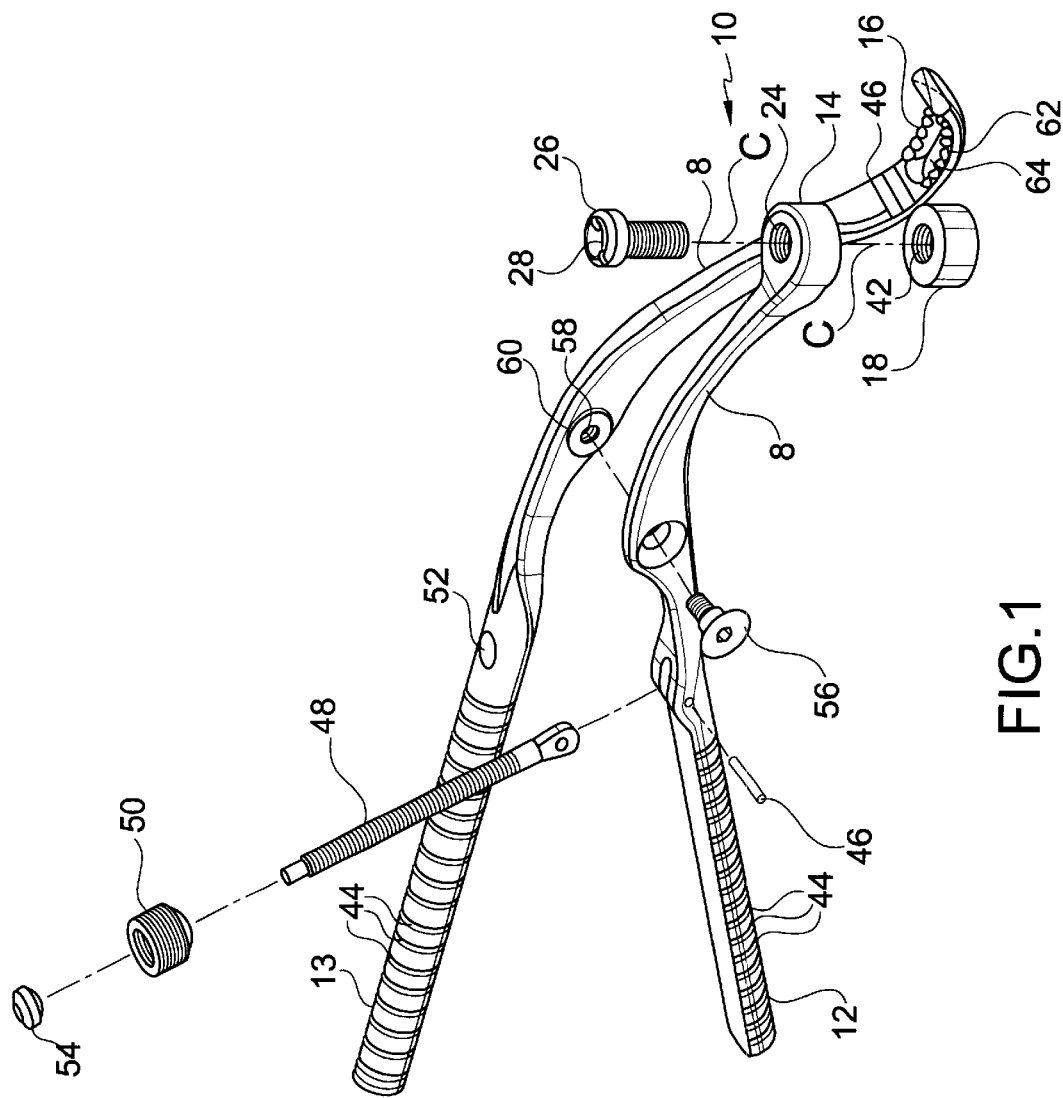
FIG. 1 is a perspective view of a clamping apparatus of the present invention.

Referring in detail to the drawings and with particular reference to FIG. 1, a clamping apparatus 10 is shown. The clamping apparatus 10 includes a pair of handles 12,13 and a pair of clamping jaws 14,16. The clamping apparatus 10 further includes means 18 for substantially reducing surface discontinuities on a support or reinforcement material 20 while enhancing friction between itself and the support material 20. The discontinuity reducing means 18 can be described as a traction material. It is contemplated that the clamping apparatus 10 of the present invention will be used to firmly secure a bone plate or support material 20 to a bone or working material 22 when performing an open reduction and internal fixation of a fracture of a bone or working material 22. While the preferred support or reinforcement material 20 includes a bone plate made out of stainless steel, other support or reinforcement materials may be made from other metals and/or metal alloys (metal mixtures). Other materials include but are not limited to aluminum, carbon, cobalt, chromium, iron, nickel, tin, titanium and zinc, or the like. It is noted that surface discontinuities include scratches and/or abrasions, and other like deformations of support or reinforcement materials.

While the working material is preferably a bone or internal skeleton of an organism, other working materials which are susceptible to increased fracturing due to loading include materials such as hard plastics, and brittle metals. Other working materials include but are not limited to ferrous alloys, non-ferrous alloys, ceramic materials, polymers and composite materials (any material susceptible to stress concentrations as a result of surface discontinuities).

The clamping apparatus 10 includes a first clamping jaw 14. The first clamping jaw 14 is disposed at a predetermined angle relative to the handle 12. This predetermined angle promotes leverage between the first clamping jaw 14 and the second clamping jaw 16. Measured from the jaw face of the first clamping jaw which is closest to the opposing jaw face of the second clamping jaw 16, the first clamping jaw is preferably disposed at an angle of 27.35° relative to the handle 12 which defines a longitudinal axis. While the predetermined angle is preferably 27.35°, other angles which further increase or decrease leverage of the clamping apparatus relative to the support material and/or the working material may be employed. For example, when the support material and working materials include fragile or brittle materials, an angle less than 27.35° may be employed to decrease the leverage of the clamping apparatus 10 relative to the support material 20 and working material 22.

The first clamping jaw 14 has a cylindrical shape end in the preferred embodiment. However, other shapes can be employed without deviating from the scope of the invention. Other shapes include, but are not limited to elliptical, triangular, rectangular, pentagonal, octagonal, hexagonal, and other polygonal shapes. The shape of the first clamping jaw 14 is typically determined by the shape of the support material 20, working material 22, and/or the discontinuity reducing means 18. The first clamping jaw 14 includes a first fastening mechanism 24 which engages with a second fastening mechanism 26. The first fastening mechanism 24 is preferably screw threads which engage with the second fastening mechanism 26 which is preferably a hollow screw. The second fastening mechanism 26 is preferably a cheese-head slotted machine screw. The first fastening mechanism 24 is not limited to screw threads, and may include other fastening structures such as adhesives, frictional engaging surfaces such as slots or projections, or other surfaces which receive fastening structures such as ball and socket joints, bearing structures, or any mechanical devices which promote fastening between two mechanical structures. Similar to the first fastening mechanism 24, the second fastening mechanism 26 is not limited to a hollow screw, and can include other fastening structures such as a smooth cylinder, a cylinder with projections which meet with corresponding frictional engaging surfaces within the first fastening mechanism 24, or other like structures.

Referring to FIG. 1 and FIG. 4B, the second fastening mechanism 26 includes an aperture 28 and a cylindrical chamber 30. The cylindrical chamber 30 has a predetermined diameter which corresponds with a diameter of a means 32 for forming an aperture in the working material 22 (see FIG. 2). The diameter of the cylindrical chamber 30 is substantially greater than the diameter of the aperture forming means 32. While the aperture 28 and cylindrical chamber 30 preferably have a circular cross-section, other cross-sectional shapes include but are not limited to triangular, rectangular, pentagonal, octagonal, hexagonal, oval, and/or elliptical shapes. The cylindrical chamber 30 substantially aligns and guides the aperture forming means 32 through the first clamping jaw 14, the discontinuity means 18, and the support material 20 in order to facilitate an appropriate angle for reaming the working material 22 with the aperture forming means 32. In the preferred embodiment, during a clamping operation, the first clamping jaw 14, which includes the first fastening mechanism 24 is substantially aligned with the second fastening mechanism, the discontinuity reducing means 18, and an aperture 34 in the support material 20.

The discontinuity reducing means 18 includes a cylindrical member which has a first chamber 36 and a second chamber 38. The first chamber 36 has a first diameter while the second chamber 38 has a second diameter which is less than the diameter of the first chamber 36. The discontinuity reducing means 18 further includes a projection 40 which is designed to engage the aperture 34 and the support material 20. The discontinuity reducing means 18 is preferably made of a non-abrasive, flexible, dielectric material such as Teflon™ (a synthetic resin polymer). However, the discontinuity reducing means 18 is not limited to Teflon™ and can include other materials which are not limited to elastomers (rubbers), thermoplastics, thermosetting polymers, and composites which include many combinations of metals, ceramics and polymers. The discontinuity reducing means 18 is substantially designed to contact support or reinforcement materials 20 which are susceptible to scratches or abrasions, or other surface discontinuities which lead to stress risers and/or stress concentrations in the vicinity of the surface discontinuities.

The side of the discontinuity reducing means 18 which engages the support or reinforcement material 20 can be contoured or shaped similar to the shape of the working material 22 or the side can have a substantially planar surface. The projection 40 is designed to engage apertures present in the support material 20. The projection 40 preferably has a frustro-conical shape; however, other shapes can be employed without deviating from the scope of the invention. Other shapes of the projection 40 include, but are not limited to, oval, elliptical, circular, triangular, rectangular, pentagonal, octagonal, hexagonal and other like shapes. The projection 40 has a pre-determined height relative to the cylindrical portion of the discontinuity reducing means 18.

The discontinuity reducing means.18 further includes a third fastening mechanism 42 that engages with the second fastening mechanism 26. The third fastening mechanism 42 preferably includes frictional engaging surfaces such as screw threads so that the discontinuity reducing means 18 is firmly mounted to the first clamping jaw 14 via a second fastening mechanism 26. The third fastening mechanism 42 is not limited to frictional engaging surfaces and can include other fastening mechanisms which are not limited to projections combined with recesses or cavities, a smooth first chamber, and predetermined projections for engaging other types of fastening mechanisms such as ball and socket joints, bearing structures, or rivets. The second chamber 38 is preferably smooth while the first chamber 36 preferably includes the third fastening mechanism 42. However, the first fastening mechanism 24 may have a smooth surface with or without an adhesive while a side of the discontinuity reducing means 18 facing the first clamping jaw 14 may include an adhesive for securely attaching the discontinuity reducing means 18 to the first clamping jaw 14. While the discontinuity reducing means 18 is preferably rigidly connected to the first clamping jaw 14, other connections where the discontinuity reducing means 18 is pivotable relative to the first clamping jaw 14 are not beyond the scope of the invention. The discontinuity reducing means 18 is designed to be removable relative to the first clamping jaw 14 in order to promote/facilitate cleaning and sterilization of the clamping apparatus. However, permanently attached discontinuity reducing means 18 relative to the first clamping jaw 14 are not beyond the scope of the present invention. The projection 40 is preferably designed as a cleat which engages at least one aperture 34 in the support material 20.

The second chamber 38 preferably has a diameter which is less than the diameter of the first chamber 36 and cylindrical chamber 30 of the second fastening mechanism 26. The diameter of the second chamber 38 is greater than the aperture forming means 32. The second chamber 38 substantially aligns and guides the aperture forming means 32 relative to the aperture 34 in the support material and a surface of the working material 22 adjacent to the support material 20. This aligning and/or guiding function of the second chamber 38 facilities the proper positioning of a reaming operation or hole making operation in the working material 22. After the hole making or reaming operation in the working material 22, the clamping apparatus 10 and the discontinuity reducing means 18 are separated from the support material 20 and the working material 22 so that a fastening mechanism may be placed in the newly formed aperture or hole in the working material 22. However, it is not beyond the scope of the present invention where the clamping apparatus 10 remains in the fixed or clamped position while a fastening mechanism is placed in the newly formed aperture or hole in the working material 22.

The aperture forming means 32 is preferably a drill which includes a rotating or revolving drill bit, which is designed to contact the working material 22. However, other hole making instruments are not beyond the scope of the present invention and can include lasers, high frequency vibrational/acoustic mechanisms, and other like hole forming instruments. The aperture forming means 32 is preferably cylindrically shaped; however, other shapes which include oval, elliptical, rectangular, triangular, pentagonal, hexagonal, octagonal, and other like polygonal shapes are not beyond the scope of the present invention. The aperture forming means 32 is preferably sized to be less than the diameter of the second chamber 38 of the projection 40 on the discontinuity reducing means 18.

Each of the handles 12, 13 include grooves 44 which substantially increase traction relative to the surface of the mechanism or user applying pressure thereto. The handles 12, 13 preferably include these grooves 44; however, other frictional engaging surfaces such as plastics or rubber but other like frictional engaging surfaces are not beyond the scope of the present invention. Each of the handles 12, 13 of the clamping apparatus 10 include a tapered portion 8 which connects each respective jaw 14, 16 to a respective handle 12, 13.

The handles 12,13 preferably include a crescent cross-sectional shape, but other cross-sectional shapes are not beyond the scope of the present invention. Other cross-sectional shapes include, but are not limited to circular, triangular, rectangular, oval, elliptical, pentagonal, hexagonal, octagonal, or other like shapes. The handle 12 of the first clamping jaw 14 preferably includes a connection pin 46 which engages with means 48 for locking each respective handle 12,13 relative to each other. The locking means 48 preferably includes a threaded spiral rod which engages with a thumb nut 50. The locking means 48 is not limited to the threaded spiral rod and can include other structures such as smooth rods with movable clamps, spring-actuated locking mechanisms, or other like structures. The connection between the handle 12 and the locking means 48 is not limited to the connection pin 46 and can include other structures such as ball and socket joints, bearing structures, or any devices which include pivotable movement between respective structures.

The thumb nut 50 preferably includes a knurled outer surface for providing a frictional engaging surface. The thumb nut 50 includes a tapered end which interfaces with an aperture 52 in the handle 13, which is coupled to the second clamping jaw 16. The thumb nut 50 further includes a threaded aperture for threadily engaging the spiral threaded rod of the locking means 48. The locking means 48 further includes a stop mechanism 54, which prohibits the thumb nut 50 from being unscrewed from the spiral rod of the locking means 48.

The handle 12 with the first clamping jaw 14 is connected to the handle 13 with the second clamping jaw 16 by a means 56 for pivoting the handle with the first clamping jaw relative to the handle 13 with the second clamping jaw 16. A means 56 for pivoting preferably includes a pivot screw which has a threaded end in addition to a frustro-conical bearing head surface. The pivoting means 56 is not limited to the pivot screw structure and can include other connection structures. Other connection structures include, but are not limited to, pin assemblies, rivets, ball and socket joints, bearing structures, or other like connecting devices.

The handle 13 with the second clamping jaw 16 includes a threaded aperture 58 for engaging with the means 56 for pivoting the handle 12 with the first clamping jaw 14. Surrounding and adjacent to the aperture 58, the handle 13 with the second clamping jaw 16 preferably includes an elevated surface 60 that facilities unobstructed movement of the handle 12 with the first clamping jaw 14 relative to the handle 13 with the second clamping jaw 16. The second clamping jaw preferably includes frictional engaging surfaces 62 such as serrated edges which are designed to engage with the working material 22. The frictional engaging surfaces 62 are designed to grip the working material 22 to prevent shifting or movement of the working material 22. The second clamping jaw 16 is not limited to the frictional engaging surfaces 62 and can include a substantially smooth surface to contact with the working material 22. The second clamping jaw 16 further includes an aperture 64 which preferably has an elliptical shape. However, the aperture 64 can include other shapes such as circular, triangular, rectangular, pentagonal, hexagonal, octagonal or other like polygonal shapes.

As stated above, the aperture 64 is designed to permit the aperture forming means 32 to penetrate therethrough without contacting the second clamping jaw 16. While the preferred embodiment of the second clamping jaw 16 includes the aperture 64, a clamping jaw 16 without an aperture where the aperture forming means 32 contacts or comes within close proximity to the second clamping jaw 16 is not beyond the scope of the present invention. The aperture 64 is designed to permit the aperture forming means 32 to penetrate through the working material 22 without contacting the second clamping jaw 16. The inner face of the second clamping jaw 16 at a position 66 is disposed at a predetermined angle relative to a longitudinal axis of the handle 13. Similar to the predetermined angle of the first clamping jaw with respect to its handle 12, the second clamping jaw 16 is disposed at a predetermined angle relative to its handle 13 to further promote leverage of the clamping apparatus 10. The preferred angle of the second clamping jaw 16 at position 66 relative to the longitudinal axis of the handle 13 is preferably 35°. However, other angles which substantially increase or decrease the amount of leverage to be applied with the clamping apparatus are not beyond the scope of the present invention. The second clamping jaw is preferably curved and includes a radius of curvature R, which approximates a circle. However, other shapes of the second clamping jaw 16 are not beyond the scope of the present invention. Other shapes of the second clamping jaw 16 include but are not limited to substantially planar contact surfaces which are parallel to the handle, gradually curved members which are substantially less than a curvature of a circle, and other like clamping jaw arrangements.

The clamping apparatus 10 of the present invention provides a method of clamping which substantially reduces formation of surface discontinuities in the support material while enhancing friction between the discontinuity reducing means 18 and the support material 20. The method steps include providing a clamping device with a first clamping jaw 14 and a second clamping jaw 16. A traction material or discontinuity reducing means 18 is attached to the first clamping jaw 14. A first side of a working material 22 is grasped with the second clamping jaw 16. The support or reinforcement material 20 is pressed against a second side of a working material 22 using the traction material 18 while the traction material substantially reduces the formation of surface discontinuities on the support material 20 while enhancing friction between the traction material 18 and the support material 20. The method further includes the step of aligning apertures within the first clamping jaw 14 with an aperture of the second fastening mechanism 26 and the aperture of the traction material 18.

The method further includes the steps of providing an attachment mechanism which includes the first fastening mechanism 24 and third fastening mechanism 42 of the traction material 18. The traction material 18 is connected to the first clamping jaw 14 with the second fastening mechanism 26 which contacts the first and third fastening mechanisms 24,42. In the alternative, the traction material 18 is fastened to the first clamping jaw 14 by an adhesive material that is placed upon mating surfaces of the first clamping jaw 14 and traction material 18.

The method of clamping further includes providing an aperture in the second fastening mechanism 26 and aligning the aperture forming mechanism 32 with the first clamping jaw 14 and the traction material 18. The aperture forming mechanism 32 is moveable through the first clamping jaw and traction material 18 within the second fastening mechanism 26. An aperture is then formed within the working material 22 by the aperture forming mechanism 32. After completion of the aperture within the working material 22, the aperture forming mechanism 32 and the clamping apparatus 10 are moved away from the support material 20 and working material 22.

With the present invention, the clamping apparatus 10 preferably holds the support material 20 relative to the working material while a plurality of apertures within the support or reinforcement material 20 are penetrated by fasteners into the working material 22. After reaming and providing fasteners in all of the plurality of apertures outside the clamping apparatus, the clamping apparatus 10 is then removed from the support material 20 and working material 22 so that the remaining aperture previously enclosed by the clamping apparatus can be penetrated with a fastener which connects to the working material 22. While the preferred embodiment of the present invention requires removal of a clamping apparatus 10 prior to placing a fastener within the aperture which is enclosed by the clamping apparatus 10, it is not beyond the scope of the present invention where the clamping apparatus 10 remains fixed relative to the support material 20 and working material 22 while a fastener is mounted through the first clamping jaw 14 and the discontinuity reducing means 18.

During clamping of the support material 20 upon the working material 22, the traction material is compressed to a second shape. However, it is not beyond the scope of the present invention where the traction material 18 does not change shape during compression thereof.

Accordingly, the present invention substantially prevents the formation of surface discontinuities on a support material while enhancing friction between the clamping apparatus and the support material. The clamping apparatus further includes mechanisms that facilitate cleaning and sterilization of the clamping apparatus. The present invention holds a support or reinforcement material in a predetermined position while maintaining adequate support for a working material to further reduce fractures that are already present in the working material. The clamping apparatus engages apertures of a support or reinforcement material and prevents slipping and movement of the support or reinforcement material while substantially reducing the size of fractures present in a working material. The method and apparatus further reduces the formation of scratches and other surface discontinuities which in turn create stress concentrations or stress risers in the vicinity of the scratches in the support material which can lead to failure of the support material.

The present invention substantially reduces surface discontinuities on a support material while enhancing friction between the discontinuity reducing mechanism and the support material. The present invention provides a method and apparatus for substantially reducing surface discontinuities on a support material while enhancing friction between such mechanism and the support material. The discontinuity reducing mechanism includes at least one of a substantially planar and a predetermined shaped surface which matches the shape of a support or reinforcement material.

The method and apparatus substantially reduce surface discontinuities on the support material while enhancing friction between the discontinuity reducing mechanism and the support material in addition to aligning an aperture forming mechanism with an aperture in the first clamping jaw, an aperture in the mechanism for substantially reducing surface discontinuities, and an aperture in a support or reinforcement material. The present invention provides a method and apparatus for clamping where the clamping apparatus can be locked into a position where a support or reinforcement material is held adjacent to a working material. The present invention provides a method and apparatus for clamping which guides the movement of an aperture forming mechanism through a support or reinforcement material in addition to a working material and through apertures in first and second clamping jaws of the clamping apparatus. The present invention provides first and second handles of a clamping apparatus which move in a smooth motion relative to each other while carrying the sheer load from a force generated from a support or reinforcement material held adjacent to a working material.

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

What is claimed is:

1. A method of clamping a support material to a working material comprising the steps of:
   providing a clamping device with a first clamping jaw and a second clamping jaw;
   providing a first fastening mechanism within an aperture of said first clamping jaw;
   providing a second fastening mechanism;
   providing a third fastening mechanism within an aperture of a traction material;
   aligning said aperture within said first clamping jaw with said aperture of said traction material;
   connecting said traction material to said first clamping jaw with said second fastening mechanism which contacts said first fastening mechanism and said third fastening mechanism;
   grasping a first side of the working material with said second clamping jaw; and
   pressing the support material against a second side of the working material with said traction material, said traction material substantially reducing formation of surface discontinuities on the support material while enhancing friction between said traction material and the support material.

2. The method of claim 1, further comprising the steps of:
   aligning an aperture forming mechanism with said first clamping jaw and said traction material;
   forming an aperture in the working material with the aperture forming mechanism; and
   attaching the support material to the working material with an attachment mechanism.

3. The method of claim 1, further comprising the step of pivoting said first clamping jaw relative to said second clamping jaw.

4. The method of claim 1, further comprising the step of placing a projection of said traction material into an aperture of the support material.

5. The method of claim 1, further comprising the steps of:
   providing an aperture in said second fastening mechanism; and
   aligning an aperture forming mechanism with said first clamping jaw and said traction material; and
   moving said aperture forming mechanism through said second fastening mechanism.

6. The method of claim 1, further comprising the step of moving an aperture forming mechanism through said first clamping jaw, said traction material, and the support material.

7. The method of claim 5, further comprising the step of moving the aperture forming mechanism out of the support material, said traction material, and said first clamping jaw.

8. The method of claim 1, further comprising the step of providing an opening in said second clamping jaw.

9. The method of claim 1, further comprising the step of locking said first clamping jaw relative to said second clamping jaw.

10. The method of claim 1, wherein said traction materials has a first shape, the method further comprising the step of compressing the traction material to a second shape.

11. A clamping apparatus for stabilizing a support material on a working material comprising;
    a first clamping jaw having a first aperture;
    a second clamping jaw;
    means for pivoting said first clamping jaw relative to said second clamping jaw;
    means for substantially reducing surface discontinuities on a support material while enhancing friction therewith, said discontinuity reducing means including a second aperture; and
    means for attaching said discontinuity reducing means to said first clamping jaw, said first aperture being substantially aligned with said second aperture, said means for attaching includes a fastening mechanism, said fastening mechanism penetrating through said first and said second apertures for guiding movement therethrough of means for forming an aperture in the working material.

12. The apparatus of claim 11, wherein said discontinuity reducing means includes a dielectric material.

13. The apparatus of claim 11, wherein said discontinuity reducing means includes a flexible material.

14. The apparatus of claim 11, wherein said fastening mechanism includes a hollow threaded fastener, said hollow threaded fastener substantially aligns means for forming a aperture in a working material and guides said aperture forming means when said aperture forming means moves through said hollow threaded fastener.

15. The apparatus of claim 11, wherein said first and second apertures include frictional engaging surfaces.

16. The apparatus of claim 15, wherein said frictional engaging surfaces include at least one of grooves and threads.

17. The apparatus of claim 11, where in said discontinuity reducing means includes a cylindrical flexible member.

18. The apparatus of claim 11, wherein said discontinuity reducing means includes a projection.

19. The apparatus of claim 18, wherein said projection includes a frustro-conical shape having a central axis substantially aligned with a central axis of said first and second apertures.

20. The apparatus of claim 18, wherein said projection includes a third aperture.

21. The apparatus of claim 18, wherein said first aperture has a first diameter, said second aperture has a second diameter, and said projection includes a third aperture having a third diameter less than said first and second diameters.

22. The apparatus of claim 11, wherein said second clamping jaw includes an opening therethrough.

23. The apparatus of claim 11, further comprising means for locking said first clamping jaw relative to said second clamping jaw.

* * * * *